(12) United States Patent
Vetter et al.

(10) Patent No.: US 6,419,656 B1
(45) Date of Patent: Jul. 16, 2002

(54) MEDICAL SYRINGE WITH BRAKED STEP-ADVANCE PLUNGER

(75) Inventors: Udo J. Vetter, Ravensburg; Klaus Schönwetter, Waldburg, both of (DE)

(73) Assignee: Arzneimittel GmbH Apotheker Vetter & Ravensburg, Ravensburg (DE)

( * ) Notice: Subject to any disclaimer, the term of this patent is extended or adjusted under 35 U.S.C. 154(b) by 0 days.

(21) Appl. No.: 09/528,513

(22) Filed: Mar. 20, 2000

(30) Foreign Application Priority Data

Mar. 19, 1999 (DE) ......................................... 199 12 322

(51) Int. Cl.[7] ................................................. A61M 3/00
(52) U.S. Cl. ............................ 604/90; 604/92; 604/211
(58) Field of Search ............................. 604/84, 90, 92, 604/210, 211

(56) References Cited

U.S. PATENT DOCUMENTS 5,080,649 A    1/1992   Vetter
5,817,056 A  * 10/1998  Tanaka et al. ................. 604/84

FOREIGN PATENT DOCUMENTS

| CH | 268694 | 5/1990 |
|----|--------|--------|
| DE | 2810370 | 9/1979 |
| EP | WO 94/13339 | 6/1994 |
| FR | 1412547 | 8/1965 |
| FR | 2024089 | 8/1970 |

\* cited by examiner

*Primary Examiner*—Gerald A. Michalsky
(74) *Attorney, Agent, or Firm*—Herbert Dubno; Andrew Wilford

(57) ABSTRACT

A medical syringe has a tubular body extending along an axis and having a front end and a rear end, a plunger axially slidable in the body and carrying a stem projecting axially rearward out of the body from the plunger, and a free piston slidable in the body forward of the plunger and subdividing the body forward of the plunger into a front compartment at the front body end and a rear compartment between the plunger and the piston. The body is formed with a bypass passage forward of the piston in a starting position so the front compartment can hold a soluble medicament and the rear compartment can hold its solvent. Structure at the rear body end forms a radially inwardly open angularly limited cutout and at least two axially spaced, angularly offset, and radially outwardly projecting stop bumps on the stem are axially displaceable through the cutout in respective angularly offset positions of the stem. The stop bumps are axially engageable against the structure except when the stem is in the respective angular position. An elastically deformable brake element engaged between the body and the stem for axially slowing axial forward advance of the stem.

10 Claims, 5 Drawing Sheets

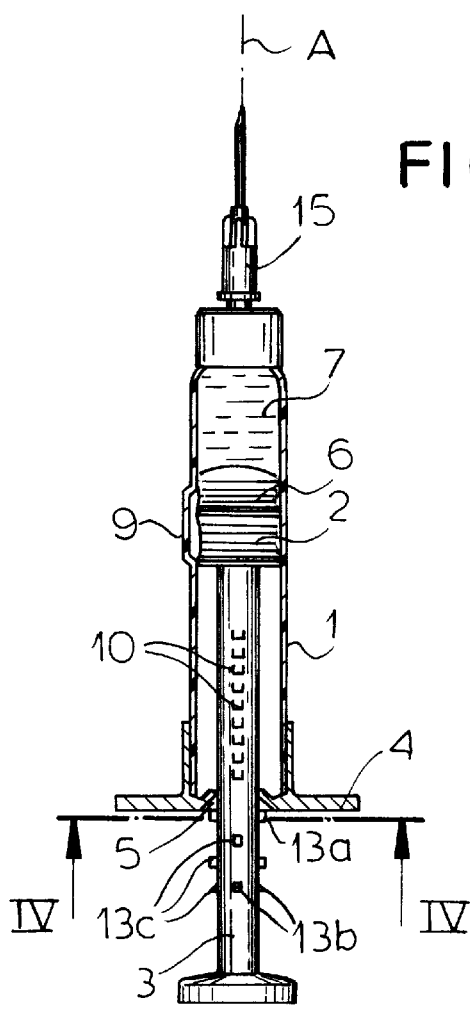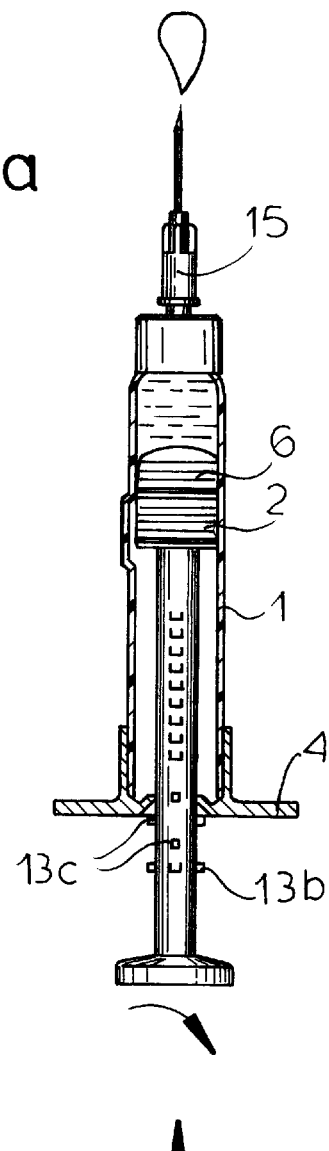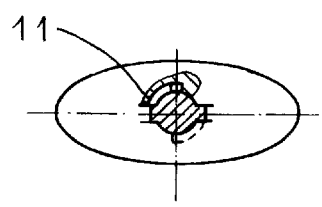

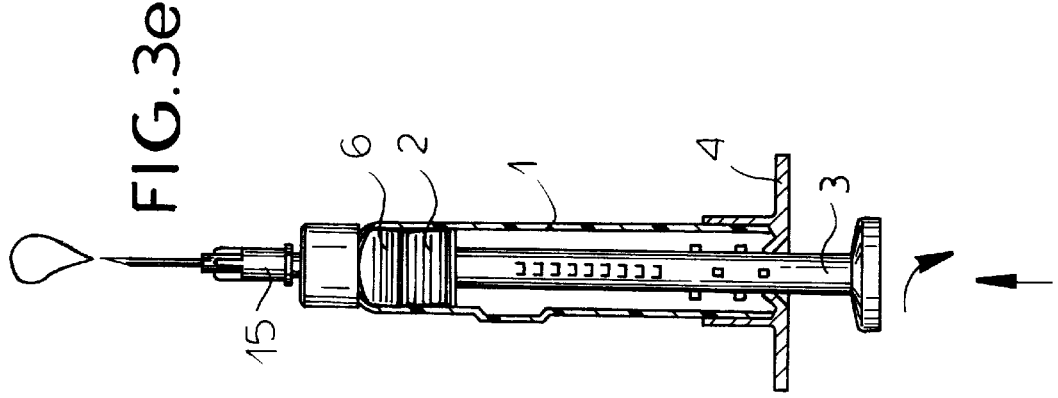
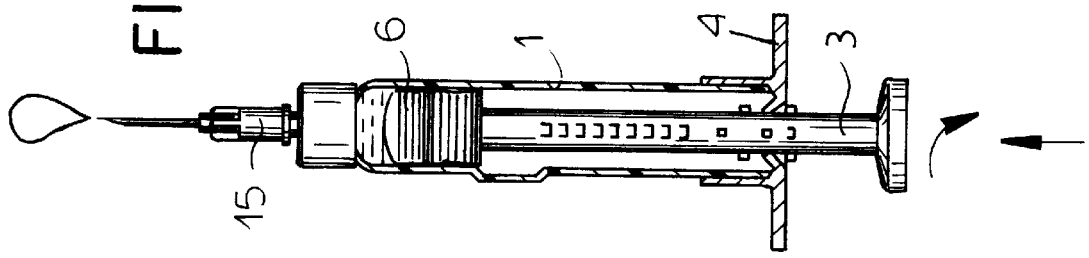
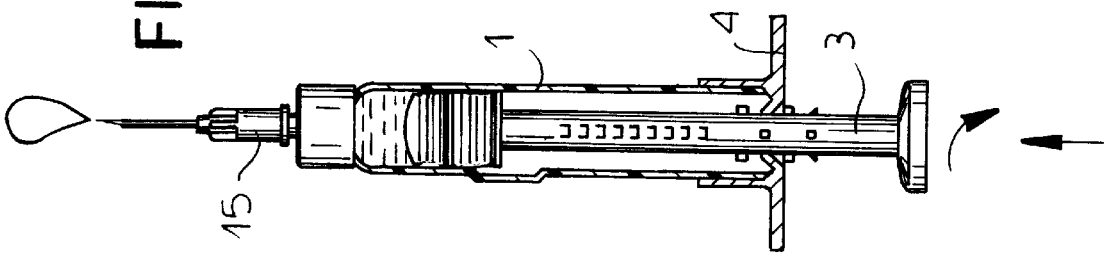

MEDICAL SYRINGE WITH BRAKED STEP-ADVANCE PLUNGER

FIELD OF THE INVENTION

The present invention relates to a medical syringe. More particularly this invention concerns such a syringe which is prefilled with a liquid and powder and which is set up for mixing the liquid and powder immediately before use.

BACKGROUND OF THE INVENTION

A standard syringe has a tubular body with a front end adapted to receive a needle or cannula and a rear end formed with radially projecting finger braces. A plunger is axially displaceable in the body and has a rod projecting axially rearwardly from the rear end so that, when the plunger is advanced, liquid is expressed through the needle mounted on the front end.

In prefilled syringes a piston is provided in the body forward of the plunger and subdivides the body in a starting position into a front compartment that is typically filled with a freeze-dried medicament powder and a rear compartment that is filled with a solvent, typically distilled water. Immediately forward of the piston in the starting position is a bypass normally formed as an inwardly open and axially extending groove. Thus when the plunger is advanced, the liquid in the rear compartment moves the piston forward until the rear end of the bypass groove is exposed in the rear compartment. Further advance of the plunger forces the liquid in the rear compartment past the piston into the front compartment where it mixes with the medicament therein. When the plunger comes to rest on the rear face of the piston and all of the liquid in the rear compartment has been driven through the bypass into the front compartment, further advance of the plunger pushes the piston forward and expresses the mixed liquid and medicament from the front end of the syringe body.

The medicament takes some time to dissolve so it is known to provide screwthreads between at least a portion of the plunger rod and the syringe body. Thus during at least the initial stages of advance of the plunger, the rod must be screwed into the syringe body ensuring slow and deliberate advance that gives the medicament time to mix and dissolve in the liquid being pumped through the bypass into the front compartment.

The problem with this system is that it takes two hands to manipulate the syringe for the mixing operation, one holding the syringe body and the other rotating the plunger. Furthermore the screwthreads make the syringe more expensive to manufacture and more difficult to assemble, unnecessarily increasing the cost of this mass-produced throw-away item.

Another difficulty with the known medical syringes is that it is frequently necessary, for instance when treating hives or dosing anesthetic, to inject carefully metered quantities of the medicament. This is typically done by providing a scale on the side of the syringe. The user must therefore be in a position to see the scale, something that is frequently impossible when an injection is actually being given, and even so it is difficult to accurately gauge the tiny plunger movements necessary to dispense the small quantities that often are needed.

OBJECTS OF THE INVENTION

It is therefore an object of the present invention to provide an improved medical syringe.

Another object is the provision of such an improved medical syringe which overcomes the above-given disadvantages, that is which makes it easy to accurately dispense small quantities of medicament.

A further object is to provide a mixer-type syringe which is of simple construction but which ensures slow and controlled mixing of the liquid and solid phases of the mixed medicament.

SUMMARY OF THE INVENTION

A medical syringe has according to the invention a tubular body extending along an axis and having a front end and a rear end, a plunger axially slidable in the body and carrying a stem projecting axially rearward out of the body from the plunger, and a free piston slidable in the body forward of the plunger and subdividing the body forward of the plunger into a front compartment at the front body end and a rear compartment between the plunger and the piston. The body is formed with a bypass passage forward of the piston in a starting position so the front compartment can hold a soluble medicament and the rear compartment can hold its solvent. Structure at the rear body end forms a radially inwardly open angularly limited cutout and at least two axially spaced, angularly offset, and radially outwardly projecting stop bumps on the stem are axially displaceable through the cutout in respective angularly offset positions of the stem. The stop bumps are axially engageable against the structure except when the stem is in the respective angular position. An elastically deformable brake element engaged between the body and the stem for axially slowing axial forward advance of the stem.

Thus with this system the brake element will prevent the plunger from advancing too rapidly, so that the solvent in the rear compartment will be pumped at a slow uniform rate around the piston through the bypass to the front compartment. The stop bumps stop advance of the piston and plunger, requiring the user to twist the piston stem to align those stop bumps striking the body rear end with the cutouts for further advance. Thus once the syringe has been fitted with a needle, cleared of air, stuck into a vein, and tested, the user can simply push down on the stem until the next set of stop bumps arrests its further advance, automatically dispensing a metered dose of the mixed medicament. A further dose can be administered once the stem is angularly indexed, and so on until the syringe is empty. The rearmost set of stop bumps includes at least one extra bump so that they define a frontmost end position for the piston and plunger.

The stop bumps according to the invention are provided in pairs with the bumps of each pair diametrically opposite each other but axially level with each other. The structure is formed with two such cutouts diametrically opposite each other. Normally each pair is offset by 90° to the preceding and following pairs.

They are spaced apart by a distance that is exactly that necessary to express a predetermined dose from the syringe. In fact the prefilled syringes can be provided with stems having differently spaced bumps, each such stem having an identifying color so that a user will know what the standard dose for a given syringe is according to its stem color. The doses can therefore be administered without looking.

The stop bumps include a frontmost stop bump that is in axial engagement with the structure when the plunger is axially forwardly engaged with the piston. Thus the user will know exactly when the rear compartment has been emptied and will not further advance the stem and waste the often valuable medicament.

The stop bumps are axially uniformly spaced along the stem and have generally radially extending end flanks. The brake element is a forwardly directed flexible lip. The cutouts can be rectangular, seen axially, or formed as sectors.

The bumps can also have angled front flanks and rear flanks extending in planes generally perpendicular to the axis, like sawteeth. The stem is formed with an axially extending row of bumps engageable with the brake element. These bumps also are of sawtooth shape with an angled front flank and a perpendicular rear flank and the element is a flexible lip extending radially inward and axially forward from the body rear end.

BRIEF DESCRIPTION OF THE DRAWING

The above and other objects, features, and advantages will become more readily apparent from the following description, reference being made to the accompanying drawing in which:

FIGS. 3a to 3e are axial sections through another syringe according to the invention as it expresses succeeding doses of mixed medicament; and FIG. 4 is a section taken along line IV—IV of FIG. 3a.

SPECIFIC DESCRIPTION

Figure 2A:
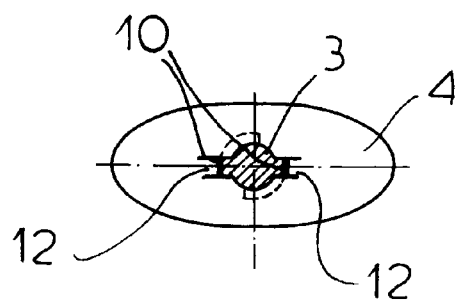
FIGS. 2a, 2b, and 2c are sections taken along respective lines IIa—IIa, IIb—IIb, and IIc—IIc of respective FIGS. 1a, 1b, and 1c.

As seen in the drawing, a syringe has a basically tubular glass or plastic body 1 centered on an axis A and slidably receiving a plunger 2. A rod or stem 3 projects axially rearward from the plunger 2 through a hole 5 in a finger-brace end cap 4. A free piston 6 subdivides the tube 1 forward of the plunger 2 into a front compartment 7 that is to start with filled with a soluble medicament, normally in powder form, and a rear compartment 8 that to start with is filled with a liquid solvent for the medicament. A radially inwardly open and axially extending bypass groove 9 is formed in the tube 1 forward of the piston 6 in the FIG. 1a starting position. Initially the front end of the tube 1 is covered by a cap 14 which is replaced for use by a needle or cannula 15.

Figure 2B:
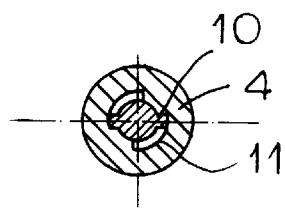
Figure 2C:
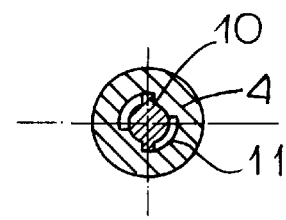

According to the invention the rod 3 is formed with two diametrically opposite and axially extending rows of radially outwardly projecting and axially uniformly spaced brake lugs 10. Each lug 10 is axially level with a diametrically opposite such lug 10 and each lug 10 has a rear flank extending perpendicular to the axis A and a front flank inclined at about 45° to the axis A, giving them a right-triangular or sawtooth shape. Seen from the end (FIGS. 2a–2c) each lug 10 is basically rectangular.

The end cap 4 on the rear end of the tube 1 is formed with diametrically opposite inwardly open cutouts 11 each extending over 90° and of a radial depth slightly greater than the radial height of the lugs 11. In addition each cutout 11 is provided with a respective radially inwardly and axially forwardly extending brake lip or tab 12 that forms with the lugs 10 a ratchet-type brake.

Figure 1A:
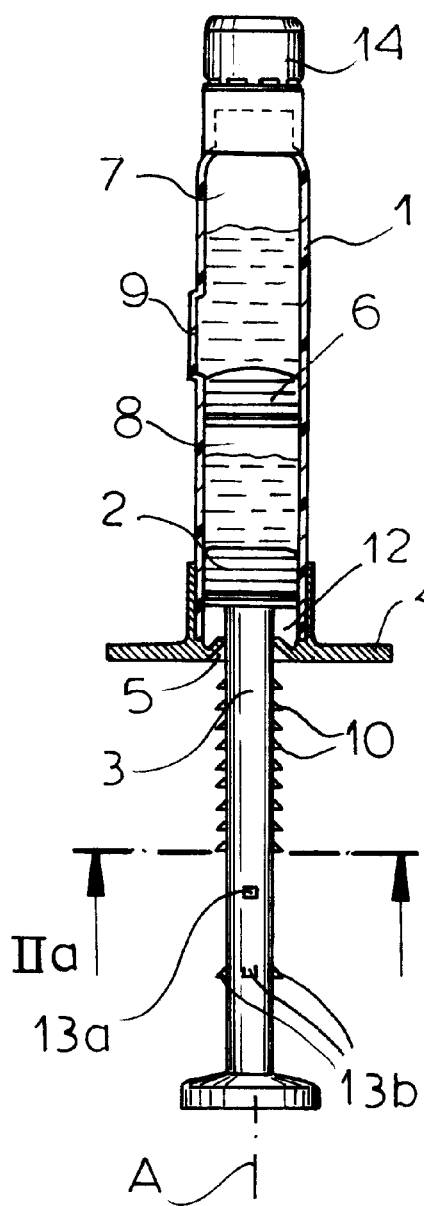
FIGS. 1a to 1f are axial sections through a syringe at succeeding steps of use.
Figure 1B:
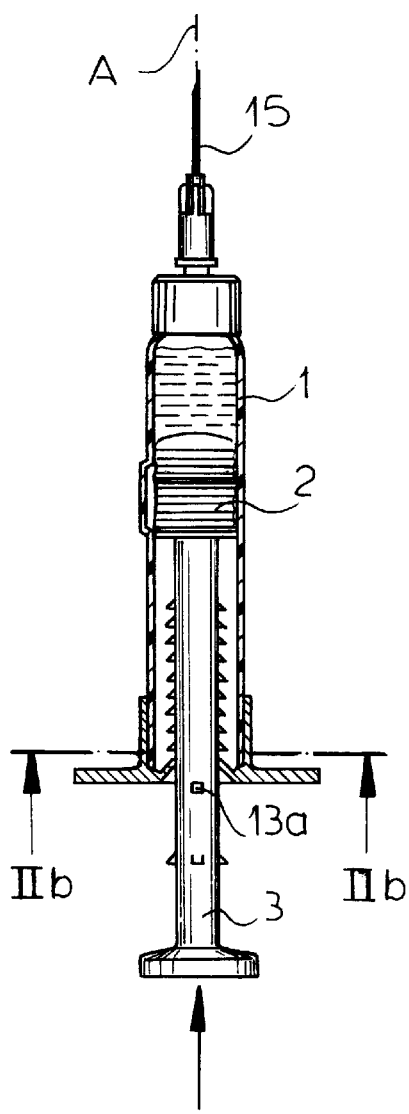

Thus as the plunger 2 is moved from the starting position of FIG. 1a to that of FIG. 1b, the liquid in the back compartment 8 will be forced through the bypass 9 to mix with the powder in the front compartment 7. As this is happening according to the invention the lugs 10 will ratchet on the tabs 12 to slow advance of the plunger 2 and thereby ensure that the liquid from the compartment 8 is pumped slowly into the front compartment 7, giving the medicament time to dissolve.

Figure 1C:
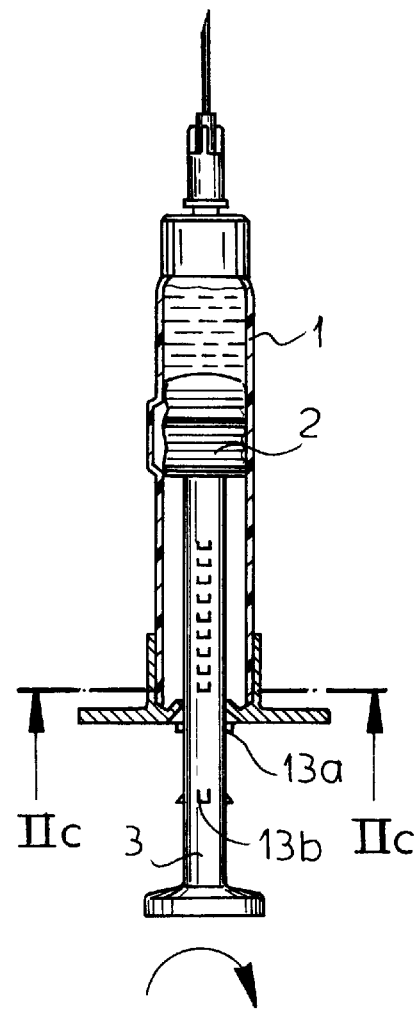
Figure 1F:
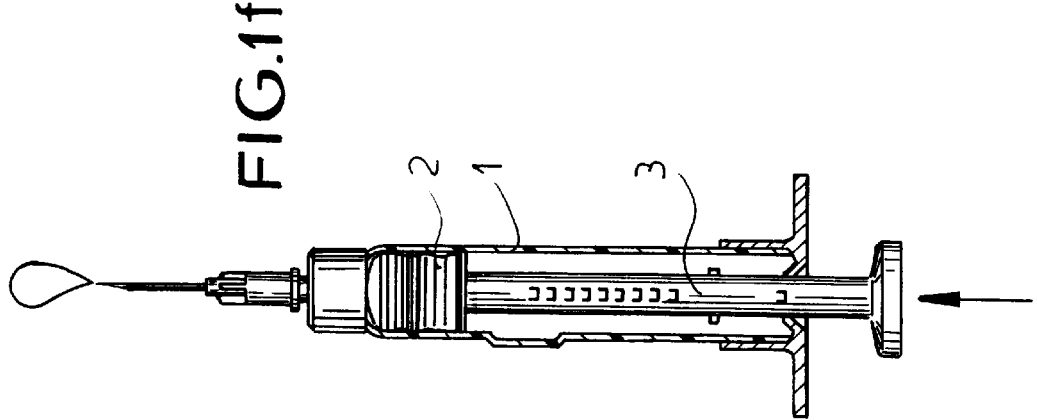
Figure 1E:
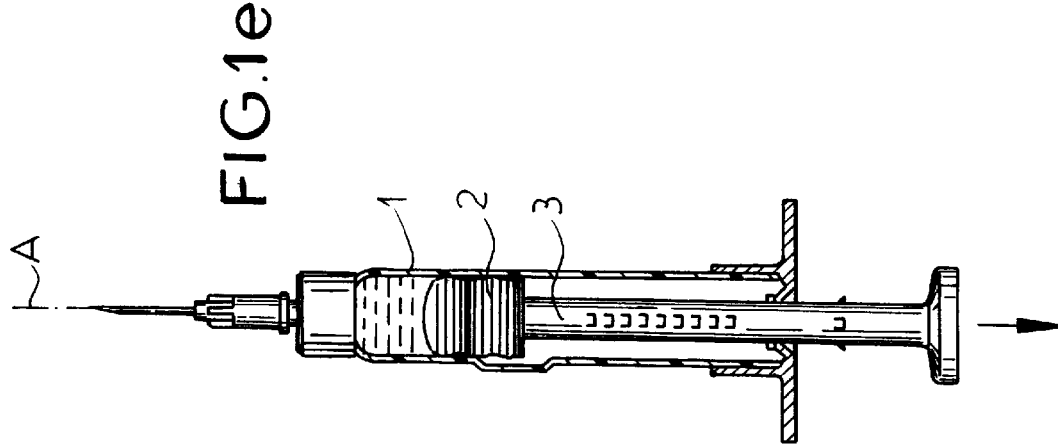
Figure 1D:
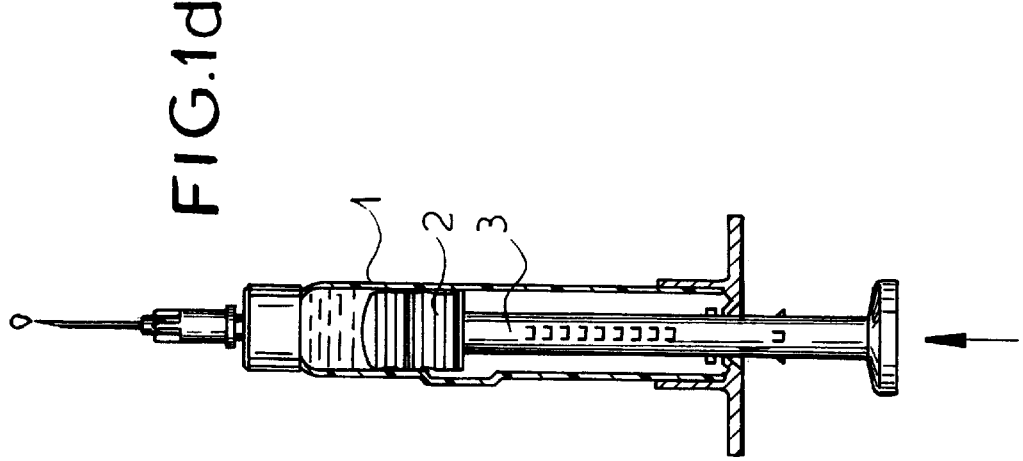

The rod 3 is formed rearward of the brake lugs 10 with two diametrically oppositely extending stop bumps 13a that are offset by 90° to the rows of lugs 10, and rearward therefrom by four more such bumps 13b angularly equis-paced about the axis A. The position of the two front stop bumps 13a is such that they abut the rear surface of the end cap 4 when the plunger 2 bottoms on the rear face of the piston 6 as shown in FIG. 1c. To advance the plunger 2 and piston 6 further, it is necessary to rotate the stem 3 through 90° so that the bumps 13a can pass through the cutouts 11. The bottoming of the front stops 13a on the finger brace 4 can be sensed by the user who will then know that the mixing operation is over and that he or she can proceed to clearing air from the syringe and actually using it. Thereafter as shown in FIG. 1d, further advance of the plunger 2 will expel the mixture from the front compartment 7 and retraction as shown in FIG. 1e will allow blood to be drawn back to insure that the stick is good.

In the system of FIGS. 3a–3f the stem 3 is formed with several intermediate pairs of stop bumps 13c, with each succeeding pair offset angularly from the pair preceding it and the pair following it. Thus each intermediate bump 13c is associated with a diametrically opposite such bump 13c that is axially level with it, and the pairs of bumps 13a, 13b, and 13c, are axially uniformly spaced. The spacing between adjacent stop-bump pairs is equal to a predetermined axial displacement of the plunger 2 which in turn expresses a predetermined volume of liquid from the tube 1. Thus the user can only advance the plunger 2 a certain distance before he or she must rotate the stem 3 through 90° to be able to advance it again through a similar distance, expressing an accurate dose of the medicament with each stepping of the piston 2. The result is extremely accurate dosing that can be done entirely by feel.

We claim:

1. A medical syringe comprising:

a tubular syringe body extending along an axis and having a front end and a rear end;

a plunger axially slidable in the body;

a stem projecting axially rearward out of the body from the plunger;

a free piston slidable in the body forward of the plunger and subdividing the body forward of the plunger into a front compartment at the front body end and a rear compartment between the plunger and the piston, the body being formed with a bypass passage;

structure at the rear body end forming a radially inwardly open angularly limited cutout;

at least two axially spaced, angularly offset, and radially outwardly projecting stop bumps on the stem axially displaceable through the cutout in respective angularly offset positions of the stem, the stop bumps being axially engageable against the structure except when the stem is in the respective angular position; and means including an elastically deformable brake element engaged between the body and the stem for axially slowing axial forward advance of the stem.

2. The medical syringe defined in claim 1 wherein the stop bumps are provided in pairs with the bumps of each pair diametrically opposite each other but axially level with each other, the structure being formed with two such cutouts diametrically opposite each other.

3. The medical syringe defined in claim 1 wherein the stop bumps are offset by about 90° to each other relative to the axis.

4. The medical syringe defined in claim 1 wherein the stop bumps include a frontmost stop bump that is in axial engagement with the structure when the plunger is axially forwardly engaged with the piston.

5. The medical syringe defined in claim 1 wherein the stop bumps are axially uniformly spaced along the stem.

6. The medical syringe defined in claim 1 wherein the brake element is a forwardly directed flexible lip.

7. The medical syringe defined in claim 1 wherein the bumps have angled front flanks and rear flanks extending in planes generally perpendicular to the axis.

8. The medical syringe defined in claim 1 wherein the stem is formed with an axially extending row of bumps engageable with the brake element.

9. The medical syringe defined in claim 8 wherein the bumps are of sawtooth shape with an angled front flank and a perpendicular rear flank and the element is a flexible lip extending radially inward and axially forward from the body rear end.

10. The medical syringe defined in claim 1 wherein the cutout has generally radially extending end flanks.

\* \* \* \* \*